United States Patent [19]

Engel et al.

[11] Patent Number: 5,296,632

[45] Date of Patent: Mar. 22, 1994

[54] CONTINUOUS REDUCTION OF A HINDERED NITRO MOIETY IN ALIPHATIC NITRO POLYAMINES

[75] Inventors: Dusan J. Engel, Barrington; Thomas P. Malloy, Lake Zurich; Steven R. Paeschke, Mt. Prospect, all of Ill.

[73] Assignee: UOP, Des Plaines, Ill.

[21] Appl. No.: 908,199

[22] Filed: Jul. 2, 1992

Related U.S. Application Data

[63] Continuation-in-part of Ser. No. 777,944, Oct. 17, 1991, abandoned.

[51] Int. Cl.$^5$ .................................... C07C 209/34
[52] U.S. Cl. .................................. 564/494; 544/384; 548/300.1; 564/448; 564/454; 564/512
[58] Field of Search ............... 564/494, 448, 454, 512

[56] References Cited

U.S. PATENT DOCUMENTS

| | | | |
|---|---|---|---|
| 2,174,498 | 9/1939 | Johnson | 564/494 |
| 2,393,825 | 1/1946 | Senkus | 564/494 |
| 3,470,250 | 9/1969 | Patterson et al. | 564/494 |
| 3,470,252 | 9/1969 | Doyle et al. | 564/494 |
| 3,917,705 | 11/1975 | Swanson et al. | 564/494 |

Primary Examiner—Richard L. Raymond
Assistant Examiner—Scott C. Rand
Attorney, Agent, or Firm—Thomas K. McBride; Eugene I. Snyder

[57] ABSTRACT

Nitro polyamines, and especially dinitro polyamines, can be readily reduced by a catalyst of zerovalent nickel on silica where the silica contains not more than 10% alumina and where the nickel content of the finished catalyst may be as high as 85%. The reductions can be performed under relatively low temperatures between 40° and 120° C. to avoid the problem of heat lability of the reactant nitro polyamines. Hydrogenations proceed with good conversion as well as good selectivity and the method offers a means of continuous hydrogenation of nitro polyamines.

16 Claims, No Drawings

CONTINUOUS REDUCTION OF A HINDERED NITRO MOIETY IN ALIPHATIC NITRO POLYAMINES

CROSS REFERENCE TO RELATED APPLICATIONS

This application is a continuation-in-part of copending application Ser. No. 07/777,944 filed Oct. 17, 1991, now abandoned, all of which is incorporated by reference.

BACKGROUND OF THE INVENTION

Certain hindered amines have been found to be especially effective light stabilizers in various coatings, in diverse fibers, and in polyurethanes. One class of these materials is characterized by the 2-oxo-1,4-piperazine ring structure where one or both carbons adjacent to N-4 are tertiary carbons, as represented by structure I, (where N-4 is the NH nitrogen),

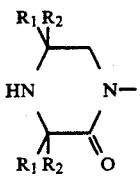

especially where all the R groups of I are methyl. Using as exemplary those compounds of structure I where all the R groups are methyls, the most facile route to the resulting oxo-piperazine structure involves the condensation of the corresponding diamine with acetone and chloroform under strongly basic conditions,

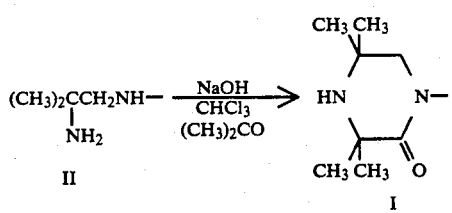

However, compounds corresponding to II and those with an analogous structure are themselves most readily prepared by reduction of the corresponding nitro amines—and thereon hangs our tale.

The nitro moiety in nitro aliphatic compounds is generally considerably more difficult to hydrogenate to the corresponding amino moiety than the nitro moiety in nitro aromatic compounds. Where the nitro aliphatic is an amino-substituted nitroalkane or nitrocycloalkane, problems are further compounded by the fact that the reactants are heat labile and sensitive to catalyst acidity. Where the nitro aliphatic is a nitro polyamine, especially one where the carbon bearing the nitro moiety is a tertiary carbon so as to afford a sterically hindered nitro moiety, the problems are still further compounded. In addition to the conversion and selectivity of hydrogenation being poor, none of the prior art methods is conducive to a continuous hydrogenation process. What is needed is a general method of continuously and rapidly reducing the sterically hindered nitro moiety attached to a tertiary carbon atom of aliphatic nitro polyamines at modest temperatures, say under 130° C., under non-acidic conditions.

There is no prior art solution to this problem. The compromise effected by the prior art is to use Raney nickel—a spongy nickel with very high hydrogenation activity formed by treating a nickel-aluminum alloy (preferably powdered) with sodium hydroxide to dissolve the aluminum—in a batch process. It will be readily appreciated that the use of powdered Raney nickel does not lend itself to a continuous process. Where grandular alloy is used, sodium hydroxide leaching leads only to a thin, surface layer of nickel, whereas the core remains unchanged nickel-aluminum alloy. In our hands, the use of such material led to extensive decomposition of aliphatic nitro compounds during attempted hydrogenation. Although one might at first surmise that another active form of nickel on a traditional catalyst support would be an acceptable substitute for Raney nickel, this was found not to be the case even though some prior art teaches these to be acceptable where the nitro moiety is not hindered and found in e.g., a nitroparaffin. In fact, we have unexpectedly found silica to be almost uniquely effective as a support for nickel in the hydrogenation of a hindered nitro moiety in an aliphatic nitro polyamine to the amino moiety, and furthermore have found that unusually high nickel loadings are required for a satisfactory catalyst. From our novel observations it is possible to devise a method of continuous hydrogenation of a sterically hindered nitro moiety in an aliphatic nitro polyamine to an amino moiety in a high yield, with good selectivity, at moderate temperatures, and with very good overall product quality.

The patentees of U.S. Pat. No. 3,470,252 have described the continuous hydrogenation of nitroparaffins with a zirconium-modified nickel on kieselguhr, and teach that either homogeneous or supported nickel catalysts may be employed. From the broad list of cited supports (kieselguhr, silica, alumina, pumice, asbestos, carbon, and silica gel) it is clear that there was no recognition of the unique effectiveness of silica as a support, an observation which is the keystone of our invention. Swanson (U.S. Pat. No. 3,917,705) teaches a plethora of metals on a multitude of supports as possible catalysts for the reduction of nitroparaffins, from which the skilled artisan could not grasp the uniqueness of our nickel on silica catalyst. Patterson et al. (U.S. Pat. No. 3,470,250) also describe the hydrogenation of nitroparaffins citing a large number of metals, including nickel and Raney nickel, and supports as suitable catalyst combinations, from which one skilled in the art can gain no appreciation of the unique effectiveness of our high-nickel on silica catalyst system. A critical feature of their invention is a multistage reduction where further hydrogenation beyond 50% conversion is conducted in the presence of ammonia. Senkus, U.S. Pat. No. 2,393,825, teaches the reduction of nitroamines where the preferred catalyst is Raney nickel. The effectiveness of Raney nickel for the hydrogenation of the nitro moiety has often been noted, but unfortunately Raney nickel does not lend itself to use in a continuous process.

SUMMARY OF THE INVENTION

The purpose of this invention is to provide a continuous process of reducing a sterically hindered nitro moiety in an aliphatic nitro polyamine to its corresponding amino moiety in high yields and selectivity. An embodiment comprises conducting the hydrogenation using a fixed bed of catalyst which is nickel dispersed on silica, where the catalyst contains from about 40% to about 85% zerovalent nickel. In a more specific embodiment the hydrogenation is performed at a temperature between about 40° and about 120° C. In a still more specific embodiment the hydrogen pressure varies between about 10 to about 1,000 psig. In yet another specific embodiment the hydrogenation is performed in an alcoholic solution of the nitro aliphatic compound containing not more than about 50 weight percent of the nitro aliphatic compound. Other embodiments and variations will be clear from the following description.

DESCRIPTION OF THE INVENTION

However effective Raney nickel may be as a catalyst in the hydrogenation of a sterically hindered nitro moiety in an aliphatic nitro polyamine to the corresponding amino moiety, it is not a process which is conducive to being practiced in other than the batch mode. One task we therefore faced was to find a satisfactory catalyst which could be used in a continuous hydrogenation process. But not only does the catalyst have to manifest those properties which render it capable of being used in a fixed bed, it also must effect the hydrogenation of a sterically hindered nitro group to the corresponding amino moiety under relatively mild reaction conditions since the nitro groups in nitro polyamines often are unstable and their decomposition tends to compete with hydrogenation when using prior art hydrogenation catalysts. Dinitro compounds are particularly difficult to work with because of their lability, and any continuous process which was devised had to operate satisfactorily with hindered dinitro aliphatic polyamines as well as the mononitro analogs. In this invention we have found a catalyst which is satisfactory in all regards and we also have developed reaction conditions which afford the reduction of hindered aliphatic nitro groups to the corresponding amino moiety in both good yield and with good selectivity.

The reactants of interest in our invention are aliphatic nitro polyamines where the nitro moiety is attached to a tertiary carbon and is therefore sterically hindered. More particularly, the reactants have the partial structure III,

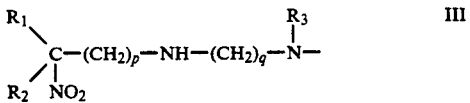

where $R_1$ and $R_2$ are alkyl groups having from 1 through about 10 carbon atoms, p is an integer, usually 1 but which may be as high as 4, and q is an integer which is usually 2 but which may range up to 6, and $R_3$ is either hydrogen, an alkyl group with 1 up to 10 carbon atoms, or a cycloalkyl moiety having from 5 to 10 carbon atoms. These reactants serve, in part, to distinguish our invention from the prior art, for the attachement of a nitro moiety to a tertiary carbon means that the nitro group is sterically hindered and that its hydrogenation will be more difficult to effect than those of the nitro group in conventional nitroparaffins. The polyamine portion of our reactants also seems to increase the lability of the nitro moiety, leading to somewhat more facile decomposition than that found in the analogous nitroparaffins. Both features are strictures which serve to place increased demands on a hydrogenation process where high conversion of the nitro to an amino moiety is desired with minimal accompanying decomposition and attending side reactions.

Of particular interest are those reactants with structures IV or V,

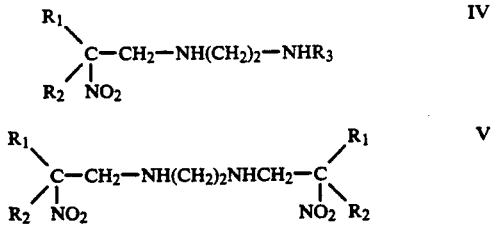

The case with $R_1 = R_2 = CH_3$ is by far the most common one and is particularly important because such structures are especially desirable in the preparation of light stabilizers. More generally, each of $R_1$ and $R_2$ may be independently selected from alkyl groups having 1 up to about 10 carbon atoms, although those with 1 through 6 carbons are the more usual ones. The moiety $R_3$ may be hydrogen, a member of the alkyl group defined above, or a cycloalkyl moiety having 5 to 10 carbon atoms, with the preferred embodiments being those where $R_3$ is either hydrogen, methyl, or cyclohexyl.

Some especially important members of this class include
1-(2'-aminoethyl)amino-2-methyl-2-nitropropane (A),
N-(2'-methylaminoethyl)amino-2-methyl-2-nitropropane ($CH_3$-amine A),
N-(2'-cyclohexylaminoethyl)amino-2-methyl-2-nitropropane,
N-(2'-methylaminoethyl)amino-2-ethyl-2-nitropropane,
N-(2'-methylaminoethyl)amino-2-propyl-2-nitropropane,
N-(2'-methylaminoethyl)amino-2-butyl-2-nitropropane,
N-(2'-methylaminoethyl)amino-2-pentyl-2-nitropropane,
N-(2'-methylaminoethyl)amino-2-methyl-2-nitrobutane,
N-(2'-methylaminoethyl)amino-2-methyl-2-nitropentane,
N-(2'-cyclohexylaminoethyl)amino-2-ethyl-2-nitropropane,
N-(2'-cyclohexylaminoethyl)amino-2-propyl-2-nitropropane,
N-(2'-cyclohexylaminoethyl)amino-2-methyl-2-nitrobutane,
N-(2'-cyclopentylaminoethyl)amino-2-methyl-2-nitropropane, and so forth.

Among the dinitro compounds a particularly important member is N,N'-bis-(2-methyl-2-nitropropyl)-1,2-ethanediamine (B).

Our choice of catalyst is the key to a successful continuous reduction process at relatively mild reaction conditions without effecting secondary reactions and/or the decomposition of the labile reactants. We have found that a catalyst of zerovalent nickel dispersed on silica as a support is quite effective. The choice of silica as a uniquely effective support is quite unexpected and arose only after several experiments showed the inadequacy of other common materials, such as alumina, as a support for nickel in the hydrogenation of aliphatic nitro compounds. Although a pure silica support in principal is the most effective one, the necessity of having a granular catalyst, for use in a fixed bed, often requires binders containing other oxides, especially alumina. Consequently it is desirable to limit the amount of alumina in the silica product to not more than 10 weight percent and an alumina content under about 8 weight percent is even more desirable.

It is also necessary that the catalyst have an unusually high percentage of nickel on the silica. In fact, a catalyst having at least 40 weight percent zerovalent nickel dispersed on a support of silica (which could contain alumina to the previously stated amount) is required in the practice of our invention. A finished catalyst containing up to about 85 weight percent zerovalent nickel may be used advantageously and catalysts containing from about 50 up to about 80 weight percent nickel are preferred.

The catalysts of our invention may be successfully prepared by depositing a suitable nickel compound on the support, converting the nickel compound to nickel oxide by calcination, and subsequently reducing the nickel oxide to zerovalent nickel. One convenient procedure for deposition of a suitable nickel compound is to make basic a slurry of a soluble nickel compound, such as nickel nitrate, and the support so as to effect formation of insoluble nickel hydroxide, which is concurrently dispersed onto the support. The support containing nickel hydroxide is then dried and subsequently calcined to convert the nickel to nickel oxide. Calcination temperatures on the order of 400° to 525° C. have been found to be adequate for this conversion at times ranging from 1 to about 5 hours. The nickel oxide then is reduced with hydrogen at a temperature from 200° up to about 450° C. Although higher temperature reductions may be carried out they are not recommended because of the accompanying agglomeration of zerovalent nickel which impairs its catalytic activity. Reduction temperatures in the range from about 325° to about 425° C. are recommended in catalyst preparation. It is not believed that the particular mode of preparation of our catalyst is critical, and other methods of preparation will be apparent to the skilled worker.

In choosing suitable reaction conditions, the key is the rapid reduction of the nitro group without excessive local heating which arises from the exothermic reaction. The nominal reaction temperature is between about 40° and about 120° C. Higher reaction temperatures, whether local or general, are discouraged because of attendant decomposition of the labile nitro compound. In some cases it has been found desirable to conduct the hydrogenation in stages. In particular, a first reduction stage may be conducted at a relatively low temperature, e.g., 40°-70° C., and a final or finishing reduction stage may be performed at the higher end of the temperature range, e.g., 100°-120° C. Hydrogen pressure is usually in the range from about 10, more often at least 50, up to about 1,000 pounds per square inch (psig). Although higher hydrogen pressures may be used in the practice of our invention no incremental benefit is to be expected thereby.

As stated previously, it is important to minimize the hot spots (local heating) arising from the reaction exotherm. One manner of doing this is to dilute the catalyst of our invention with inert particles. Such inert particles act as a heat sink, thus dissipating the heat throughout a larger mass and thereby minimizing localized heating, but it is important to understand that the reaction centers still contain an abnormally high loading of zerovalent nickel dispersed on silica which is unchanged by dilution. It also is important to realize that the dilution of, for example, a 70% nickel on silica catalyst 1:1 with inert material is not the equivalent of using a catalyst of 35% nickel on silica. In the former case one has an effective catalyst with good heat transport to minimize localized heating, while in the latter case one has a relatively poor catalyst which simply does not effect hydrogenation in the desired manner.

Another means of minimizing local heating arising from the reaction exotherm is to dilute the nitro polyamine with a solvent. Alcohols are particularly good solvents to use as diluents, especially alcohols containing from 1 to 5 carbon atoms, and particularly those containing 1 to 4 carbons, that is, methanol, ethanol, propanol, and isopropyl alcohol. However desirable alcohols may be as a solvent to control the effects of the reaction exotherm, they are not unique as a class of solvents. What is needed are materials that are good solvents for the nitro polyamine being reduced (therefore moderately polar organic materials) while remaining completely inert under the conditions of the hydrogenation. Such materials as ethers and, to a somewhat lesser extent, esters exemplify moderately polar classes of organic compounds which may be suitable for use as solvents in this invention. It is desired that the solution of the nitro polyamine contain less than 50 weight percent of the nitro polyamine, although not less than about 10 weight percent, and it is even more desirable that there be present less than 25 weight percent of the nitro polyamine. Our experience is that optimal results generally are achieved when the solutions contain between about 10 and about 25 weight percent of the nitro polyamine.

Hydrogenations may be readily carried out continuously by flowing a nitro polyamine over a packed bed of the catalyst of this invention at hydrogenation conditions. More specifically, the nitro polyamine is passed over the solid catalyst, preferably downflow although an upflow mode may be used without necessarily equivalent results, which has been diluted somewhat with inert particles to minimize localized heating. The nitro polyamine is preferably dissolved in a moderately polar organic material, such as an alcohol containing from 1 to 5 carbon atoms, and solutions containing from about 10 to about 50 weight percent of the nitro compound, more desirably between about 10 and 25 weight percent, are used as the feedstock. The temperature in the reaction zone is maintained between about 40° and 120° C., with the lower temperatures favored to reduce decomposition and unwanted side reactions. A quite favorable variant uses a 2-stage reduction, where the first stage of reduction is performed at a temperature under about 70° C. and where a final or finishing hydrogenation may be effected at 100°-120° C. Hydrogen pressures from about 10, more usually at least 50, to about 1,000 psig may be employed.

The following examples only illustrate our invention and are not intended to be limited thereto. Only the major features of our invention are exemplified below, and other variants will be recognized by the skilled artisan as being well within the scope of our invention.

EXAMPLE 1

Preparation of Catalyst. To a solution of 418.8 grams of nickel nitrate hexahydrate dissolved in 1 liter distilled water (pH 2.2) was added 37.5 g of Ludox TM AS-40 (pH 8.2) containing 40% silica. A solution of 138 g of sodium hydroxide in 150 mL water (pH 11.0) was added to the nickel/silica solution rapidly with good stirring, after which the resulting slurry was stirred for another 2 hours. Solids were collected by filtration and washed with 2 liters distilled water. After the filter pack was dried at 100° C., the solid was redispersed in water and solids were washed until the filtrate was pH 8.0. Solids again were collected and dried at 100° C., then extruded as 1/16-inch extrudates using Ludox TM as the binder. The extrudates were calcined to 500° C. in air to convert the nickel to its oxide, and then reduced in situ at 400° C. with a 4 volume percent hydrogen in nitrogen stream. Chemical analysis of the extrudates showed a nickel oxide content of 87 weight percent, which corresponds to a nickel content in the final catalyst of 84 weight percent.

In some instances the catalyst was zerovalent nickel on silica purchased from United Catalysis, Inc. as C-46-7-RS, which was activated prior to its use by treatment in flowing hydrogen at 400° C. as described above.

EXAMPLE 2

Preparation of Illustrative Nitro polyamines. To a solution of 78.9 g of ethylenediamine (99% purity; 1.3 moles) in 65 g isopropyl alcohol contained in a three-neck flask equipped with a blade stirrer, condenser, nitrogen inlet, sample port, thermometer, and formaldehyde addition auger was added 103.2 g of 2-nitropropane (95% pure; 1.1 mole) over a ten-minute period with a concomitant 15° C. temperature rise. The mixture was cooled to 35° C. and paraformaldehyde (95% pure, as prills; 31.6 g; 1.0 mole) was added in 18 equal portions spaced at ten-minute intervals. The temperature was maintained at 40°±2° C. After paraformaldehyde addition was complete, the reaction mixture was stirred for 3 hours at 40° C., then stored at room temperature overnight. Typical analysis showed 28.9% isopropyl alcohol, 12.6% ethylenediamine, 11.3% 2-nitropropane, 35.1% nitro polyamine A, 6.9% nitroamine B, 2.1% of cy-A, and 1.8% cy-B, whose structures are given below. The material was refrigerated until hydrogenated.

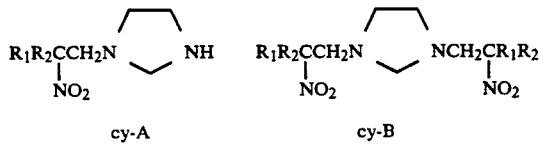

cy-A           cy-B

EXAMPLE 3

Batch hydrogenation of nitro polyamines. 2 grams of the catalyst (powder or extrudate) in a tube placed within a vertical furnace was treated in a flowing hydrogen stream (1-2 SCFH) at 400° C. for 2 hours. After the catalyst had slowly cooled to room temperature it was discharged directly into a 300 cc hydrogenation rocking reactor liner containing 25 g of nitro polyamine solution. The catalyst addition was done under continuous hydrogen flow to avoid contact with air. The reactor then was sealed, purged with hydrogen, and hydrogenation was generally performed in 2 stages, the first at 40° C., 150 psig hydrogen for 5 hours and the second at 120° C., 1,000 psig hydrogen for 1 hour.

EXAMPLE 4

Continuous hydrogenation of nitro polyamines. An intimate mixture of 80 cc of catalyst extrudates and 80 cc of a low surface area high silica carrier used as a diluent was placed in a vertical reactor tube. Hydrogen flow was adjusted to 6 SCFH and the reactor was brought to 400° C. and maintained there for 4 hours to effect a complete reduction of nickel to zerovalent stage. After the catalyst had cooled to 50° C., the nitro polyamine solution was pumped downflow at a LHSV of 2 at 50°-60° C. and 1,000 psig hydrogen at a flow of 6 SCFH, and the product was collected.

EXAMPLE 5

Effect of temperature of nickel oxide reduction. This set of experiments was designed to show the effect of reducing the nickel oxide on silica at different temperatures. Reductions were carried out in a 300 cc stainless steel rocker with a glass liner using 25 g of a solution of nitro polyamine in isopropyl alcohol (30 weight percent alcohol) with the nitro polyamine composition, exclusive of unchanged reactants (see Example I) being 67% A, 12% B, 5% cy-A, and 14% cy-B. A first stage hydrogenation at 40° C. and 150 psig hydrogen for 5 hours was followed by a second stage at 120° C. and 1,000 psig hydrogen for 1 hour. Results are summarized in Table 1. The structures of the various products, amine A, amine B, cy-amine A, cy-amine B, $CH_3$-amine A, and $CH_3$-amine B, follow

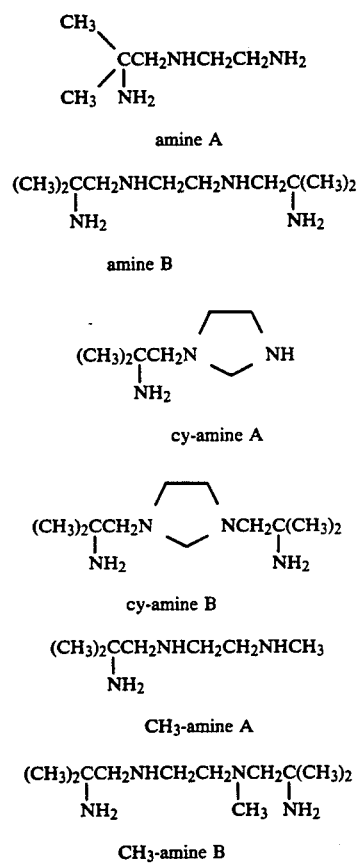

TABLE 1

Effect of NiO Reduction Temperature on Catalyst Activity and Selectivity

| Run | $1^a$ | $2^a$ | $3^b$ | $4^b$ | $5^b$ |
|---|---|---|---|---|---|
| T° C. | 200 | 400 | 400 | 450 | 500 |
| Time (hr) | 2 | 2 | 2 | 8 | 2 |
| % $H_2{}^c$ | 100 | 100 | 4 | 4 | 4 |
| Conversion % | 100 | 100 | 100 | 100 | 100 |
| Selectivi- | | | | | |

TABLE 1-continued

Effect of NiO Reduction Temperature on Catalyst Activity and Selectivity

| Run | 1[a] | 2[a] | 3[b] | 4[b] | 5[b] |
|---|---|---|---|---|---|
| ties %[d] | | | | | |
| Amine A | 32.2(41.4) | 58.6(67.5) | 69.8(76.3) | 65.8(71.4) | 69.2(75.5) |
| CH3-amine A | 5.9(6.9) | 5.4(5.6) | 7.8(7.7) | 4.6(4.5) | 7.4(7.3) |
| Cy-amine A | .6(0.7) | .3(0.3) | .8(0.8) | 11.7(11.6) | 2.4(2.4) |
| Amine B | 47.6(39.7) | 31.1(23.3) | 17.0(12.1) | 8.1(5.7) | 11.2(7.9) |
| CH3-amine B | 1.3(1.0) | .4(0.3) | .4(0.3) | 2.5(1.7) | .7(0.5) |
| Cy-amine B | .6(0.5) | 1.5(1.1) | 1.1(0.7) | .9(0.6) | 1.3(0.9) |
| Others | 11.8(9.8) | 2.6(2.0) | 3.1(2.2) | 6.4(4.5) | 7.8(5.5) |
| Amines A & B | 79.8(81.1) | 89.7(90.8) | 86.8(88.4) | 73.9(77.1) | 80.4(83.4) |

[a]Feedstock is a 70% weight percent solution in isopropyl alcohol of a nitro polyamine mixture consisting of 67% A, 12% B, 5% cy-A, and 14% cy-B, (exclusive of unchanged reactants).
[b]Feedstock is a 70% weight percent solution in methanol of a mixture of nitro polyamines consisting of 53% A, 34% B, 6% cy-A, and 6% cy-B, (exclusive of unchanged reactants).
[c]Percent hydrogen in a hydrogen-nitrogen mixture used to reduce NiO.
[d]Values outside parentheses are weight percent selectivity; values inside parentheses are mole percent selectivity.

EXAMPLE 6

Effect of support on catalyst activity. Several samples of zerovalent nickel were used as catalyst in a batch hydrogenation to determine the effect of support material (where used) in hydrogenation. As the data of Table 2 clearly show, silica is uniquely effective as a support.

TABLE 2

Effect of the Support on the Activity of Nickel Catalyst in the Hydrogenation of 1-(2'-aminoethyl)amino-2-methyl-2-nitropropane[a]

| Catalyst | Support | T° C. | $P_{psig}H_2$ | Conv. %[g] | Selectivity[h] Amine A | cy-Amine A | Amine B | cy-amine B |
|---|---|---|---|---|---|---|---|---|
| Raney-Ni, Powder[b] | None | 40/120 | 300/600 | 100 | 88 (92) | 1 (1) | 8 (5) | 2 (1) |
| Raney-Ni, Granules[c] | Al | 120 | 600 | 90 | Hydrogenolysis + Degradation | | | |
| 56% NiO/SiO2 | SiO2 | 120 | 600 | 100 | 89 (92) | 2 (2) | 7 (5) | 0 (0) |
| 50% Ni/Kieselguhr[d] | Kieselguhr | 120 | 600 | 84 | 78 (80) | 17 (16) | 1 (1) | 0 (0) |
| 25% Ni/Al2O3[e] | Al2O3 | 60 | 1500 | 95 | 62 (67) | ←—Unknown—→ | | |
| 15% Ni/Al2O3[f] | Al2O3 | 100 | 1500 | 100 | 64 (69) | Product decomposed | | |

[a]See Examples 3 and 5 for reaction conditions. Feedstock was a methanol solution (18% by weight methanol) of the following amine mixture: A, 88%; B, 7%; cy-A, 2%; cy-B, 2%.
[b]From Aldrich Co.
[c]Davison Chemicals, W. R. Grace.
[d]Engelhard Ni-3266.
[e]Available from UOP.
[f]HTC-400, from Crossfield Catalysts, U.K.
[g]Conversion of nitro groups to amino groups
[h]Values outside parentheses are weight percent selectivity; values inside parentheses are mole percent selectivity.

EXAMPLE 7

Effect of solvent dilution. Batch reactions were performed in a 300 cc stainless steel rocker with a glass liner using 25 g of a nitro polyamine solution and 2 g of catalyst under reaction conditions identical to that described in the foregoing example. The feedstock was an isopropyl alcohol solution (30 weight percent alcohol) containing unchanged reactants and a mixture of nitro polyamines consisting of 67% A, 12% B, 5% cy-A, and 14% cy-B. Results are tabulated in Table 3. The data in the table show that dilution profoundly influences product distribution and, to a somewhat lesser extent, also increases the formation of the total of amine A and amine B.

TABLE 3

Effect of Solvent Dilution

| | Weight Percent Isopropyl Alcohol | | |
|---|---|---|---|
| | 30 | 60 | 80 |
| Conversion % | 100 | 100 | 100 |
| Selectivities %[a] | | | |
| Amine A | 80.0(84.5) | 62.4(70.0) | 43.5(53.6) |
| CH3-amine A | 6.8(6.4) | 9.0(9.1) | 4.3(4.8) |
| Cy-amine A | .2(0.2) | .5(0.4) | 0(0) |
| Amine B | 9.4(6.4) | 21.0(15.3) | 52.2(41.7) |
| CH3-amine B | .2(0.1) | .9(0.6) | 0(0) |
| Cy-amine B | .9(0.6) | 1.2(0.8) | 0(0) |
| Others | 2.5(1.7) | 5.1(3.7) | 0(0) |
| Amines A + B | 89.4(90.9) | 83.4(85.3) | 95.7(95.3) |
| Amines A/B | 8.5(13.2) | 3.0(4.6) | .8(1.3) |

[a]Values outside parentheses are weight percent selectivity; values inside parentheses are mole percent selectivity

EXAMPLE 8

Effect of solvent, solvent dilution, and catalyst dilution. The effect of both the solvent and solvent dilution was determined in a continuous flow fixed bed reactor using a catalyst of this invention. The results, which are summarized in Table 4, suggest that isopropyl alcohol had a somewhat modest beneficial effect relative to methanol, but again demonstrates the advantages of performing the reduction in a highly diluted medium. All hydrogenations were performed at 80° C. and afforded 100% of nitro polyamine conversion. No product composition could be determined for reduction in 30% methanol because of extensive decomposition.

TABLE 4

Effect of Solvent and Solvent Dilution in Continuous Flow Fixed Bed Reactor

| | 30% MeOH | 60% MeOH | 60% IPA[a] | 80% IPA[a] |
|---|---|---|---|---|
| H2(psig) | 1000 | 1000 | 500 | 1000 |
| LHSV | 2 | 2 | 1 | 2 |
| H2 SCFH | 4.5 | 4.5 | 3 | 6 |
| Conversion, % | 100 | 100 | 100 | 100 |
| Selectivities, %[b] | | | | |
| Amine A | | 41.5(50.1) | 44.9(52.3) | 42.5(50.9) |
| CH3-amine A | | 13.2(14.4) | 9.7(10.2) | 9.4(10.2) |
| Cy-amine A | | .4(.4) | 10.3(11.0) | 5.4(5.9) |
| Amine B | | 6.4(5.0) | 6.5(4.9) | 37.0(28.7) |
| CH3-amine B | | .5(.4) | .6(.4) | 2.8(2.0) |
| Cy-amine B | | .7(.6) | 0(0) | 0(0) |
| Others | | 37.2(29.1) | 28.0(21.2) | 2.9(2.3) |
| Amines A + B | | 47.9(55.1) | 51.4(57.2) | 79.5(79.6) |

TABLE 4-continued
Effect of Solvent and Solvent Dilution in Continuous Flow Fixed Bed Reactor

|  | 30% MeOH | 60% MeOH | 60% IPA[a] | 80% IPA[a] |
| --- | --- | --- | --- | --- |
| Amines A/B |  | 6.50(10.0) | 6.90(10.7) | 1.15(1.8) |

[a]IPA = isopropyl alcohol.
[b]Values outside parentheses are weight percent selectivity; values inside parentheses are mole percent selectivity.

Table 5 summarizes the effect of catalyst dilution with a low surface area silica carrier containing more than 95% silica. Although conversion of the nitro polyamine in the starting mixture in all cases was complete, dilution has an important effect on the total amount of amine A and amine B which is formed as well as a significant effect on the ratio of amine A to amine B. Note that in each case the feedstock was a mixture of nitro polyamines dissolved in an alcohol (80 weight percent). All reductions were performed at a pressure of 1,000 lbs hydrogen with a LHSV of 2 and a hydrogen flow of 6 SCFH.

TABLE 5
Effect of Catalyst Dilution in Continuous Flow Fixed Bed Reactor

|  | Undiluted |  | Diluted 1:1 |
| --- | --- | --- | --- |
| T° C. | 80 | 80 | 60 |
| % Conversion | 100 | 100 | 100 |
| Nitro polyamines Selectivities, %[a] |  |  |  |
| Amine A | 42.5(50.9) | 52.7(61.8) | 53.9(63.5) |
| CH3-amine A | 9.4(10.2) | 7.4(7.8) | 4.5(4.8) |
| Cy-amine A | 5.4(5.9) | 0(0) | 0(0) |
| Amine B | 37.0(28.7) | 38.7(29.4) | 41.3(31.5) |
| CH3-amine B | 2.8(2.0) | 0(0) | 0(0) |
| Cy-amine B | 0(0) | 0(0) | 0(0) |
| Others | 2.9(2.3) | 1.3(1.0) | 0.3(0.2) |
| Amines A + B | 79.5(79.6) | 91.4(91.2) | 95.2(95.0) |
| Amines A/B | 1.2(1.8) | 1.4(2.1) | 1.3(12.0) |

[a]Values outside parentheses are weight percent selectivities; values inside parentheses are mole percent selectivities.

What is claimed is:

1. A method for the continuous conversion of a nitro moiety in a nitro polyamine having the structure X or Y

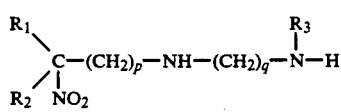

-continued

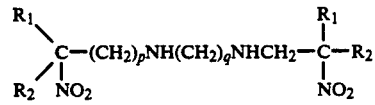

to the corresponding primary amino moiety comprising hydrogenating the nitro moiety by flowing a liquid mass of the nitro polyamine over a solid mass of a catalyst consisting essentially of from about 40 to about 85 weight percent zerovalent nickel dispersed on a support of silica at a temperature from about 40° to about 120° C. and at a partial hydrogen pressure from about 10 up to about 1000 pounds per square inch and recovering the hydrogenated product, where $R_1$ and $R_2$ are independently selected from the group consisting of alkyl groups containing from 1 up to about 10 carbon atoms, p is an integer from 1 up to about 4, q is an integer from 2 up to about 6, and $R_3$ is hydrogen, an alkyl group containing from 1 up to about 10 carbon atoms, or a cycloalkyl group containing from 5 up to about 10 carbon atoms.

2. The method of claim 1 where $R_1$ and $R_2$ each are independently selected from the group consisting of alkyl groups containing from 1 through 6 carbon atoms.

3. The method of claim 1 where $R_1$ and $R_2$ each are methyl groups.

4. The method of claim 1 where q is 2.

5. The method of claim 1 where p is 1.

6. The method of claim 1 where each of $R_1$ and $R_2$ are methyl groups, p is 1, and q is 2.

7. The method of claim 1 where the nitro polyamine is N,N'-bis-(2-methyl-2-nitropropyl)-1,2-ethanediamine.

8. The method of claim 1 where the nitro polyamine is 1-(2'-aminoethyl)amino-2-methyl-2-nitropropane.

9. The method of claim 1 where the nitro polyamine is 1-(2'-methylaminoethyl)amino-2-methyl-2-nitropropane.

10. The method of claim 1 where the nitro polyamine is 1-(2'-cyclohexylaminoethyl)amino-2-methyl-2-nitropropane.

11. The method of claim 1 where the support of silica contains not more than about 10 weight percent of alumina.

12. The method of claim 1 where the support of silica contains not more than about 8 weight percent of alumina.

13. The method of claim 1 where the aliphatic nitro compound is present as a 10 to 50 weight percent solution in a moderately polar organic solvent.

14. The method of claim 13 where the organic solvent is an alcohol containing from 1 to 5 carbon atoms.

15. The method of claim 1 further characterized in that the solid mass of catalyst is diluted with inert particles.

16. The method of claim 1 where the catalyst contains from 50 up to 80 weight percent nickel.

* * * * *